United States Patent [19]

Yoshimura et al.

[11] Patent Number: 4,578,472
[45] Date of Patent: Mar. 25, 1986

[54] 2,2,6,6-TETRAMETHYLPIPERIDINE AND ITS PRODUCTION

[75] Inventors: Masakatsu Yoshimura, Sakai; Takeo Fujii; Shinichi Yachigo, both of Toyonaka; Tamaki Ishii, Suita, all of Japan

[73] Assignee: Sumitomo Chemical Company, Limited, Osaka, Japan

[21] Appl. No.: 610,818

[22] Filed: May 15, 1984

[30] Foreign Application Priority Data

May 27, 1983 [JP] Japan .................. 58-94467
Aug. 1, 1983 [JP] Japan .................. 58-141737

[51] Int. Cl.⁴ .................................. C07D 211/36
[52] U.S. Cl. ........................... 546/188; 252/403; 524/103
[58] Field of Search ............. 252/403; 546/190, 188; 524/103

[56] References Cited

U.S. PATENT DOCUMENTS

| | | | |
|---|---|---|---|
| 3,850,877 | 11/1974 | Cook | 546/190 X |
| 3,971,795 | 7/1976 | Cook | 546/190 X |
| 4,191,683 | 3/1980 | Brunetti et al. | 252/403 X |
| 4,198,334 | 4/1980 | Rasberger | 252/403 X |
| 4,316,837 | 2/1982 | Molt et al. | 546/190 X |
| 4,415,688 | 11/1983 | Minagawa et al. | 524/103 X |

FOREIGN PATENT DOCUMENTS

| | | | |
|---|---|---|---|
| 0077862 | 5/1983 | Japan | 546/190 |
| 0603642 | 4/1978 | U.S.S.R. | 546/190 |

*Primary Examiner*—Richard D. Lovering
*Attorney, Agent, or Firm*—Wenderoth, Lind & Ponack

[57] ABSTRACT

There is provided a 2,2,6,6-tetramethylpiperidine derivative represented by the formula (I), wherein $R_1$ and $R_2$ independently represent a hydrogen atom or methyl group, and $R_3$ represents an alkylene group having one to four carbon atoms. A method for producing said derivatives is also provided.

18 Claims, No Drawings

2,2,6,6-TETRAMETHYLPIPERIDINE AND ITS PRODUCTION

The present invention relates to a 2,2,6,6-tetramethylpiperidine derivative represented by the formula (I),

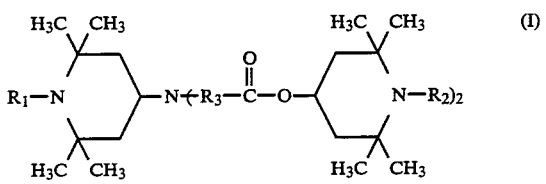

wherein $R_1$ and $R_2$ independently represent a hydrogen atom or methyl group, and $R_3$ represents an alkylene group having one to four carbon atoms, its production and a stabilizer for synthetic resins containing it as an effective ingredient.

It is hitherto well known that synthetic resins such as polyethylene, polypropylene, polyvinyl chloride, polyurethane, ABS resin, etc. deteriorate by the action of light, thereby showing a remarkable reduction in physical properties followed by phenomena such as softening, brittleness, discoloration and the like.

For the purpose of preventing such deterioration by light, to use various photostabilizers is conventional. Such photostabilizers include for example 2-hydroxy-4-methoxybenzophenone, 2-hydroxy-4-n-octoxybenzophenone, 2-(2-hydroxy-5-methylphenyl)benzotriazole, 2-(2-hydroxy-3-tert-butyl-5-methylphenyl)-5-chlorobenzotriazole, 2-(2-hydroxy-3,5-dipentylphenyl)benzotriazole, ethyl 2-cyano-3,3-diphenylacrylate, 2,4-di-tert-butylphenyl 3,5-di-tert-butyl-4-hydroxybenzoate, [2,2'-thiobis(4-tert-octylphenolate)]n-butylamine.-nickel(II), Ni salt of bis(3,5-di-tert-butyl-4-hydroxybenzylphosphoric acid)monoethyl ester, bis(2,2,6,6-tetramethyl-4-piperidyl)sebacate and the like. These photostabilizers, however, are not yet quite satisfactory in terms of light fastness, when used alone or in combination of sulfur-containing antioxidant(s).

The present inventors extensively studied to solve these problems, and as a result, found that 2,2,6,6-tetramethylpiperidine derivatives having a specified structure represented by the above formula (I) have an excellent effect in preventing synthetic resins from deterioration by light. The present inventors thus attained the present invention.

The 2,2,6,6-tetramethylpiperidine derivative represented by the above formula (I) is a novel compound unknown to the literatures first synthesized by the present inventors, and it can be produced by reacting a 4-amino-2,2,6,6-tetramethylpiperidine compound represented by the formula (II),

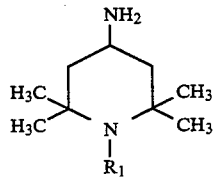

wherein $R_1$ represents a hydrogen atom or methyl group, with a halogenated carboxylic acid or ester represented by the formula (III),

wherein X represents a halogen atom, $R_3$ represents an alkylene group having one to four carbon atoms, and $R_4$ represents a hydrogen atom or lower alkyl group, and then reacting the resulting reaction product with a 4-hydroxy-2,2,6,6-tetramethylpiperidine compound represented by the formula (IV),

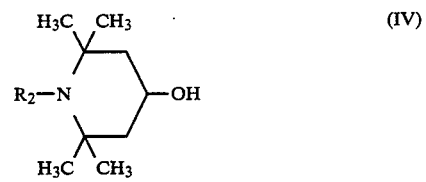

wherein $R_2$ represents a hydrogen atom or methyl group, in the presence of a basic catalyst.

In the first-step reaction of this method, the molar ratio of 4-amino-2,2,6,6-tetramethylpiperidine compound represented by the formula (II) to halogenated carboxylic acid represented by the formula (III) is generally 1 to 1.5–3, preferably 1 to 2–2.5. This reaction proceeds without a catalyst, but it is preferred to use inert organic solvents such as toluene, xylene, etc. Also, dehydrohalogenating agents as represented by triethylamine, pyridine, etc. may be used. The reaction temperature is 10° to 150° C., preferably 10° to 100° C.

The halogenated carboxylic acid used as a material in this reaction includes for example monochloroacetic acid, monobromoacetic acid, 3-chloropropionic acid, 3-bromopropionic acid, 4-chlorobutyric acid, 4-bromobutyric acid, 5-chlorovaleric acid, 5-bromovaleric acid and the lower alkyl esters thereof (e.g. methyl, ethyl, propyl and butyl esters). Particularly, the lower alkyl esters of the halogenated carboxylic acids are preferably used.

The second-step reaction is carried out by reacting the reaction product resulting from the above first step with a 4-hydroxy-2,2,6,6-tetramethylpiperidine compound represented by the formula (IV) in the presence of a basic catalyst. In this reaction, the reaction solution after completion of the first-step reaction may be used as it is, or the reaction product separated from it may be used.

In this reaction, the amount of 4-hydroxy-2,2,6,6-tetramethylpiperidine compound used is generally 1.5 to 4 times by mole, preferably 2 to 2.5 times by mole based on the 4-amino-2,2,6,6-tetramethylpiperidine compound which is a starting material.

This reaction proceeds without a solvent, but it is preferred to use inert organic solvents such as methanol, toluene, xylene, etc. As the basic catalyst, there may be used, for example, potassium hydroxide, sodium hydroxide, lithium hydroxide, lithium aluminum hydride, sodium boron hydride, sodium hydride, lithium hydride, sodium amide, sodium tert-butoxide, potassium tert-butoxide, sodium methoxide, potassium methoxide, sodium phenoxide, potassium phenoxide, metallic sodium, metallic potassium and the like. Of these, potassium tert-butoxide, sodium methoxide, sodium phenoxide and sodium hydroxide are preferably used. The amount of the catalyst used is 0.01 to 1 time by mole, preferably 0.1 to 0.5 time by mole based on the 4-amino- 2,2,6,6-tetramethylpiperidine compound which is a starting material.

The reaction temperature is 0° to 150° C., preferably 10° to 50° C.

Typical 2,2,6,6-tetramethylpiperidine derivatives thus produced are shown in Table 1. In the method of the present invention, the monoester derivative is sometimes formed together with the diester derivative, which is an objective compound of the present invention, depending upon the reaction conditions to obtain a mixture of the both esters. But, this mixture may be used as such without special problems for uses as stabilizers, etc.

TABLE 1

$$R_1-N\underset{H_3C\ CH_3}{\overset{H_3C\ CH_3}{\diagdown\diagup}}N+R_3-\overset{O}{\underset{\|}{C}}-O-\underset{H_3C\ CH_3}{\overset{H_3C\ CH_3}{\diagdown\diagup}}N-R_2)_2$$

| Compound No. | $R_1$ | $R_2$ | $R_3$ |
|---|---|---|---|
| 1-1 | H | H | $CH_2$ |
| 1-2 | H | $CH_3$ | $CH_2$ |
| 1-3 | $CH_3$ | $CH_3$ | $CH_2$ |
| 1-4 | H | H | $CH_2CH_2$ |
| 1-5 | H | H | $CH_2CH_2CH_2$ |
| 1-6 | H | H | $CH_2CH_2CH_2CH_2$ |

When the 2,2,6,6-tetramethylpiperidine derivative according to the present invention is used as a stabilizer, the amount of the derivative blended with synthetic resins is generally 0.01 to 5 parts by weight, preferably 0.05 to 2 parts by weight based on 100 parts by weight of the synthetic resins. For blending them, the well-known apparatus and methods for incorporating stabilizers, pigments, fillers, etc. in synthetic resins may be used almost as such.

In the application of the stabilizer for synthetic resins of the present invention, other additives such as antioxidants, photostabilizers, metal sequestering agents, metal soaps, nucleating agents, lubricants, antistatic agents, flame retardants, pigments, fillers and the like may be used together with said stabilizer.

Particularly, the thermal stability and oxidation stability of synthetic resins can be improved by using a phenol antioxidant together. This phenol antioxidant includes for example 2,6-di-tert-butyl-4-methylphenol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 1,3,5-tris[β-(3,5-di-tert-butyl-4-hydroxyphenyl)propionyloxyethyl]isocyanurate, 1,3,5-tris(2,6-di-methyl-3-hydroxy-4-tert-butylbenzyl)isocyanurate, pentaerythritol tetrakis[β-(3,5-di-tert-butyl-4-hydroxyphenyl)propionate] and the like.

Also, the color can be improved by using a phosphite antioxidant.

The phosphite antioxidant includes for example tris(nonylphenyl)phosphite, distearyl pentaerythritol diphosphite, tris(2,4-di-tert-butylphenyl)phosphite, tris(2-tert-butyl-4-methylphenyl)phosphite, bis(2,4-di-tert-butylphenyl)-pentaerythritol diphosphite, tetrakis(2,4-di-tert-butylphenyl)-4,4'-biphenylene diphosphite and like.

Further, in case of conventional hindered amine type light stabilizers, when used in combination with sulfur-containing antioxidants which are known to improve antioxidant properties, their light-resistance performance is remarkably decreased. In contrast thereto, in case of the compounds of this invention, such decrease in the light-resistant performance is much less and therefore they can effectively used in combination of known sulfur-containing antioxidants. Examples of such sulfur-containing antioxidants are dilauryl thiodipropionate, dimyristyl thiodipropionate, distearyl thiodipropionate, pentaerythritol tetrakis(β-laurylthiopropionate), pentaerythritol tetrakis(β-hexylthiopropionate), etc.

As synthetic resins stabilized by the stabilizer for synthetic resins of the present invention, there are given for example low-density polyethylene, high-density polyethylene, linear low-density polyethylene, chlorinated polyethylene, EVA resin, polypropylene, polyvinyl chloride, methacrylic resin, polystyrene, impact-resistant polystyrene, ABS resin, AES resin, MBS resin, polyethylene terephthalate, polybutylene terephthalate, polyamide, polyimide, polycarbonate, polyacetal, polyurethane, unsaturated polyester resin and the like.

Next, the present invention will be illustrated in detail with reference to the following examples, which are not however to be interpreted as limiting the invention thereto.

EXAMPLE 1

Production of Compound 1-1

A solution of 10.0 g (0.064 mole) of 4-amino-2,2,6,6-tetramethylpiperidine in 60 ml of toluene was kept at 60° C., 16.1 g (0.13 mole) of ethylmonochloroacetate was added over 10 minutes, and the solution was then kept at 80° C. for 1 hour. After completion of the reaction, the reaction solution was washed with an aqueous saturated sodium hydrogencarbonate solution and then with water, and the toluene layer was concentrated to obtain 19.7 g of a transparent oily liquor.

4.6 Grams (0.014 mole) of this oily liquor and 5.1 g (0.032 mole) of 4-hydroxy-2,2,6,6-tetramethylpiperidine were dissolved in 50 ml of methanol, and 1.2 g (0.0064 mole) of 28% sodium methylate was added to the resulting solution which was then refluxed for 2 hours.

After completion of the reaction, the solvent was removed by evaporation, and the residue was diluted with 30 ml of toluene and poured into 30 ml of ice water. After phase separation and washing with water, the solvent was removed by evaporation to obtain a pale brown crude crystal. This crude crystal was recrystallized from an ethyl acetate/hexane mixed solvent to obtain 6.9 g (purity 80%) of a white crystal. Upon 3 recrystallizations from n-hexane there was obtained the desired product in the form of white crystals (purity 97.5%, m.p. 108°–109° C.).

Molecular ion peak of mass spectrum, 550.

H'-NMR spectrum: δ=5.2(t, 2H), 3.6(s, 4H), 3.2(t, 1H), 1.9(d, 4H), 1.8(d, 2H), 1.2(m, 45H).

Elementary analysis (as $C_{31}H_{58}N_4O_4$):

| | C | H | N |
|---|---|---|---|
| Found (%) | 67.70 | 10.70 | 10.05 |
| Calculated (%) | 67.58 | 10.63 | 10.17 |

EXAMPLE 2

Production of Compound 1-3

10.0 Grams (0.059 mole) of 1-methyl-4-amino-2,2,6,6-tetramethylpiperidine was dissolved in 60 ml of toluene and reacted with 16.1 g (0.13 mole) of ethyl monochloroacetate in the same manner as in Example 1. The reaction solution obtained was similarly after-treated to obtain 17.7 g of a transparent oily liquor.

4.8 Grams (0.014 mole) of this oily liquor was reacted with 5.5 g (0.032 mole) of 1-methyl-4-hydroxy-2,2,6,6-tetramethylpiperidine and then purified in the same manner as in Example 1 to obtain 7.8 g of a white crystal which was an objective matter.

Yield, 82%; m.p., 85°–88° C.
Molecular ion peak of mass spectrum, 592.
Elementary analysis (as $C_{34}H_{64}N_4O_4$):

|  | C | H | N |
|---|---|---|---|
| Found (%) | 62.56 | 9.80 | 9.61 |
| Calculated (%) | 62.78 | 9.88 | 9.45 |

EXAMPLE 3

Production of Compound 1-5

10.0 Grams (0.064 mole) of 4-amino-2,2,6,6-tetramethylpiperidine was dissolved in 60 ml of toluene and reacted with 19.6 g (0.13 mole) of ethyl 4-chlorobutyrate in the same manner as in Example 1. The reaction solution obtained was similarly after-treated to obtain 21.6 g of a transparent oily liquor.

5.0 Grams (0.014 mole) of this oily liquor was reacted with 5.1 g (0.032 mole) of 4-hydroxy-2,2,6,6-tetramethylpiperidine and then purified in the same manner as in Example 1 to obtain 7.0 g of a white crystal which was an objective matter.

Yield, 80%; m.p., 90°–93° C.
Molecular ion peak of mass spectrum, 592.
Elementary analysis (as $C_{34}H_{64}N_4O_4$):

|  | C | H | N |
|---|---|---|---|
| Found (%) | 62.89 | 9.70 | 9.40 |
| Calculated (%) | 62.78 | 9.99 | 9.45 |

EXAMPLE 4

The following blend was mixed on a mixer for 5 minutes and then melt-kneaded at 180° C. on a mixing roll to obtain a compound. This compound was then formed into a sheet of 1 mm in thickness on a hot press kept at 210° C. to prepare a test piece of 150×30×1 mm in size.

This test piece was exposed to light in a Sunshine weather-O-meter (light source, carbon arc; temperature of black panel, 83°±3° C.; spraying cycle, 120 minutes; spraying time, 18 minutes) and folded as a lobster every 60 hours to obtain the time required for the test piece to break into two. The weathering resistance was evaluated by this time.

Further, there was prepared a test piece of 40×40×1 mm. In a Geer oven at 160° C. the time until 30% of the test piece area has become brittle has been measured. The time was defined as "Induction period to embrittlement", by which the heat and oxidation stability was evaluated.

The result is shown in Table 2.

Compounding:

|  | Part by weight |
|---|---|
| Unstabilized polypropylene | 100 |
| Calcium stearate | 0.1 |
| 2,6-Di-tert-butyl-4-methylphenol | 0.05 |

Test compound shown in Table 2.

In the table, UVA-1 to AO-2 mean the following compounds:

UVA-1: 2-Hydroxy-4-methoxybenzophenone
UVA-2: 2-Hydroxy-4-n-octoxybenzophenone
UVA-3: 2-(2-Hydroxy-5-methylphenyl)benzotriazole
UVA-4: 2-(2-Hydroxy-3-tert-butyl-5-methylphenyl)-5-chlorobenzotriazole
UVA-5: 2-(2-Hydroxy-3,5-dipentylphenyl)benzotriazole
UVA-6: Ethyl 2-cyano-3,3′-diphenylacrylate
UVA-7: Nickel salt of bis(3,5-di-tert-butyl-4-hydroxybenzyl phosphoric acid)monoethyl ester
UVA-8: Bis(2,2,6,6-tetramethyl-4-piperidyl)sebacate
AO-1: Tris(3,5-di-tert-butyl-4-hydroxybenzyl)isocyanurate
AO-2: Dilauryl-3,3′-thiodipropionate

TABLE 2

| Test compound | Example | | | | | | | | | | | |
|---|---|---|---|---|---|---|---|---|---|---|---|---|
|  | 1 | 2 | 3 | 4 | 5 | 6 | 7 | 8 | 9 | 10 | 11 | 12 |
| 1 - 1 | 0.2 | | | | | | 0.2 | | | | | |
| 1 - 2 | | 0.2 | | | | | | 0.2 | | | | |
| 1 - 3 | | | 0.2 | | | | | | 0.2 | | | |
| 1 - 4 | | | | 0.2 | | | | | | 0.2 | | |
| 1 - 5 | | | | | 0.2 | | | | | | 0.2 | |
| 1 - 6 | | | | | | 0.2 | | | | | | 0.2 |
| AO - 1 | | | | | | | 0.05 | 0.05 | 0.05 | 0.05 | 0.05 | 0.05 |
| AO - 2 | | | | | | | 0.25 | 0.25 | 0.25 | 0.25 | 0.25 | 0.25 |
| Weathering resistance (hour) | 2220 | 2160 | 2040 | 2160 | 2100 | 1980 | 1920 | 1860 | 1740 | 1860 | 1800 | 1680 |
| Induction period to embrittlement (hour) | 60 | 60 | 55 | 60 | 55 | 55 | 780 | 715 | 680 | 710 | 690 | 675 |

| Test compound | Comparative example | | | | | | | | | | | | | | | | |
|---|---|---|---|---|---|---|---|---|---|---|---|---|---|---|---|---|---|
|  | 13 | 14 | 15 | 16 | 17 | 18 | 19 | 20 | 21 | 22 | 23 | 24 | 25 | 26 | 27 | 28 | 29 |
| UVA - 1 | 0.2 | | | | | | | 0.2 | | | | | | | | | No addi- |
| UVA - 2 | | 0.2 | | | | | | | | 0.2 | | | | | | | |

TABLE 2-continued

| | | | | | | | | | | | | | | | | |
|---|---|---|---|---|---|---|---|---|---|---|---|---|---|---|---|---|
| UVA - 3 | | | 0.2 | | | | | | 0.2 | | | | | | | tion |
| UVA - 4 | | | | 0.2 | | | | | | 0.2 | | | | | | |
| UVA - 5 | | | | | 0.2 | | | | | | 0.2 | | | | | |
| UVA - 6 | | | | | | 0.2 | | | | | | 0.2 | | | | |
| UVA - 7 | | | | | | | 0.2 | | | | | | 0.2 | | | |
| UVA - 8 | | | | | | | | 0.2 | | | | | | 0.2 | | |
| AO - 1 | | | | | | | | | 0.05 | 0.05 | 0.05 | 0.05 | 0.05 | 0.05 | 0.05 | 0.05 |
| AO - 2 | | | | | | | | | 0.25 | 0.25 | 0.25 | 0.25 | 0.25 | 0.25 | 0.25 | 0.25 |
| Weathering resistance (hour) | 180 | 420 | 240 | 600 | 420 | 240 | 360 | 1800 | 240 | 480 | 360 | 720 | 480 | 240 | 420 | 960 | 120 |
| Induction period to embrittlement (hour) | 20 | 30 | 20 | 45 | 30 | 20 | 30 | 30 | 480 | 490 | 480 | 500 | 490 | 480 | 485 | 485 | 5 |

EXAMPLE 5

To a 25% urethane dope (comprising 25 parts of a polyurethane resin, 3.75 parts of dimethylformamide and 71.25 parts of tetrahydrofuran) was added each of the test compounds shown in Table 3 in a rate of 1% based on the above polyurethane resin. The mixture was coated onto polyester film in a thickness of 1.2 mm and dried for 1 hour in a dryer kept at 45° C. The sheet thus obtained was punched into No. 3 dumbbell test pieces. The test piece were exposed to light for 60 hours and 120 hours in a fade-O-meter (light source: ultraviolet carbon arc, temperature of blackpanel: 63°±3° C.), and a percent retention of break strength was obtained by the tensile test (tensile rate: 200 mm/mm, measurement temperature: 25° C.).

The result is shown in Table 3.

TABLE 3

| Test Compound | Example | | | | | | | | | | | | Comparative example | | | | | | |
|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 |
| 1 - 1 | 1 | | | | | | 0.7 | | | | | | | | | | | | No addition |
| 1 - 2 | | 1 | | | | | | 0.7 | | | | | | | | | | | |
| 1 - 3 | | | 1 | | | | | | 0.7 | | | | | | | | | | |
| 1 - 4 | | | | 1 | | | | | | 0.7 | | | | | | | | | |
| 1 - 5 | | | | | 1 | | | | | | 0.7 | | | | | | | | |
| 1 - 6 | | | | | | 1 | | | | | | 0.7 | | | | | | | |
| UVA - 2 | | | | | | | | | | | | | 1 | | | 0.7 | | | |
| UVA - 5 | | | | | | | | | | | | | | 1 | | | 0.7 | | |
| UVA - 8 | | | | | | | | | | | | | | | 1 | | | 0.7 | |
| AO - 1 | | | | | | | 0.05 | 0.05 | 0.05 | 0.05 | 0.05 | 0.05 | | | | 0.05 | 0.05 | 0.05 | |
| AO - 2 | | | | | | | 0.25 | 0.25 | 0.25 | 0.25 | 0.25 | 0.25 | | | | 0.25 | 0.25 | 0.25 | |
| Percent retention of break strength | 60 hrs. | 85 | 82 | 78 | 81 | 79 | 72 | 81 | 78 | 74 | 77 | 75 | 70 | 43 | 56 | 66 | 41 | 53 | 56 | 30 |
| | 120 hrs. | 65 | 60 | 56 | 59 | 57 | 47 | 62 | 57 | 53 | 56 | 54 | 45 | 22 | 30 | 40 | 21 | 28 | 33 | 16 |

EXAMPLE 6

The blend described below was melt-kneaded on a mixing roll kept at 150° C. and then formed into a sheet of 0.5 mm in thickness on a hot press kept at 160° C.

This sheet was exposed to light for 1200 hours in a Sunshine weather-O-meter (light source: carbon arc, temperature of black panel: 63°±3° C., spraying cycle: 120 minutes, spraying time: 18 minutes), and the degree of discoloration was observed.

The result is shown in Table 4.

Compounding:

| | Part by weight |
|---|---|
| Polyvinyl chloride | 100 |
| Dioctyl phthalate | 38 |
| Epoxidized soybean oil | 2 |
| Barium stearate | 1 |
| Zinc stearate | 0.3 |
| Test compound | 0.2 |

TABLE 4

| | No. | Test compound | Degree of discoloration |
|---|---|---|---|
| Example | 1 | 1-1 | Pale yellow |
| | 2 | 1-2 | Pale yellow |
| | 3 | 1-3 | Pale yellow |
| | 4 | 1-4 | Pale yellow |
| | 5 | 1-5 | Pale yellow |
| | 6 | 1-6 | Pale yellow |
| Comparative example | 7 | UVA - 2 | Brown spot |
| | 8 | UVA - 3 | Yellow |
| | 9 | UVA - 8 | Yellow |
| | 10 | No addition | Blackish brown |

What is claimed is:

1. A 2,2,6,6-tetramethylpiperidine derivative represented by the formula (I),

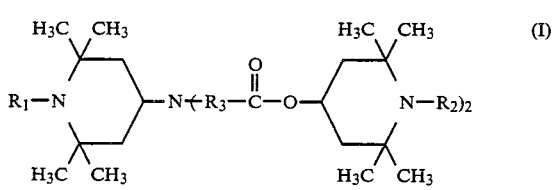

wherein $R_1$ and $R_2$ independently represent a hydrogen atom or methyl group, and $R_3$ represents an alkylene group having one to four carbon atoms.

2. The 2,2,6,6-tetramethylpiperidine derivative as described in claim 1, wherein $R_1$ and $R_2$ are a hydrogen atom.

3. The 2,2,6,6-tetramethylpiperidine derivative as described in claim 1, wherein the substituent $R_3$ is —$CH_2$—, —$CH_2CH_2$—, —$CH_2CH_2CH_2$— or —$CH_2CH_2CH_2CH_2$—.

4. The 2,2,6,6-tetramethylpiperidine derivative as described in claim 3, wherein $R_1$ and $R_2$ are a hydrogen atom.

5. The 2,2,6,6-tetramethylpiperidine derivative as described in claim 1, wherein the substituent $R_3$ is —$CH_2$—.

6. The 2,2,6,6-tetramethylpiperidine derivative as described in claim 2, wherein the substituent $R_3$ is —$CH_2$—.

7. A method for producing a 2,2,6,6-tetramethylpiperidine derivative represented by the formula (I),

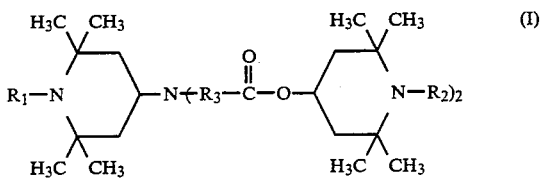

wherein $R_1$ and $R_2$ independently represent a hydrogen atom or methyl group, and $R_3$ represents an alkylene group having one to four carbon atoms, wherein a 4-amino-2,2,6,6-tetramethylpiperidine compound represented by the formula (II),

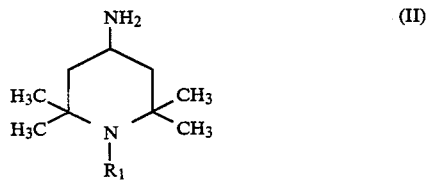

wherein $R_1$ has the same meaning as above, is reacted with a halogenated carboxylic acid or ester represented by the formula (III),

wherein X represents a halogen atom, $R_3$ has the same meaning as above, and $R_4$ represents a hydrogen atom or lower alkyl group, and then the resulting reaction product is reacted with a 4-hydroxy-2,2,6,6-tetramethylpiperidine compound represented by the formula (IV),

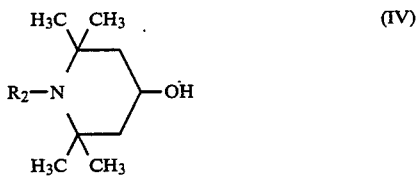

wherein $R_2$ has the same meaning as above, in the presence of a basic catalyst, wherein the molar ratio of the compound of formula (II) to the acid of formula (III) is 1 to 2.5 and wherein the molar ratio of the compound of formula (IV) is 2 to 2.5 times amount of the compound of formula (II).

8. The method as described in claim 7, wherein in the first-step reaction, an inert organic solvent is used.

9. The method as claimed in claim 8, wherein the inert organic solvent is toluene or xylene.

10. The method as described in claim 7, wherein in the first-step reaction, the reaction temperature is 10° to 100° C.

11. The method as described in claim 7, wherein the halogenated carboxylic acid or ester represented by the formula (III) is monochloroacetic acid, monobromoacetic acid, 3-chloropropionic acid, 3-bromopropionic acid, 4-chlorobutyric acid, 4-bromobutyric acid, 5-chlorovaleric acid, 5-bromovaleric acid or lower alkyl esters thereof.

12. The method as claimed in claim 11, wherein the lower alkyl ester is the methyl, ethyl, propyl or butyl ester.

13. The method as described in claim 7, wherein in the second-step reaction to react the reaction product resulting from said first-step reaction with a 4-hydroxy-2,2,6,6-tetramethylpiperidine compound represented by the formula (IV) in the presence of a basic catalyst, the reaction product is used after separated from the reaction solution or without being separated therefrom.

14. The method as described in claim 13, wherein the basic catalyst used in the second-step reaction is sodium hydroxide, potassium hydroxide, lithium hydroxide, lithium aluminum hydride, sodium boron hydride, sodium hydride, lithium hydride, sodium amide, sodium tert-butoxide, potassium tert-butoxide, sodium methoxide, potassium methoxide, sodium phenoxide, potassium phenoxide, metallic sodium or metallic potassium.

15. The method as described in claim 14, wherein the amount of the catalyst used is 0.1 to 0.5 time by mole based on the 4-amino-2,2,6,6-tetramethylpiperidine compound represented by the formula (II).

16. The method as described in claim 13, wherein the reaction temperature is 10° to 50° C.

17. The method as described in claim 7, wherein in the second-step reaction, an inert organic solvent is used.

18. The method as claimed in claim 17, wherein the inert organic solvent is methanol, toluene or xylene.

* * * * *